(12) United States Patent
Grey

(10) Patent No.: US 7,271,117 B2
(45) Date of Patent: *Sep. 18, 2007

(54) EPOXIDATION CATALYST

(75) Inventor: Roger A. Grey, West Chester, PA (US)

(73) Assignee: Lyondell Chemical Technology, L.P., Greenville, DE (US)

( * ) Notice: Subject to any disclaimer, the term of this patent is extended or adjusted under 35 U.S.C. 154(b) by 350 days.

This patent is subject to a terminal disclaimer.

(21) Appl. No.: 10/870,124

(22) Filed: Jun. 17, 2004

(65) Prior Publication Data

US 2005/0282699 A1 Dec. 22, 2005

(51) Int. Cl.
*B01J 29/06* (2006.01)

(52) U.S. Cl. .................. 502/66; 502/60; 502/62; 502/64; 502/71; 502/74; 502/77

(58) Field of Classification Search .............. 502/60, 502/62, 64, 66, 74, 71, 77
See application file for complete search history.

(56) References Cited

U.S. PATENT DOCUMENTS

| | | | |
|---|---|---|---|
| 3,351,635 A | 11/1967 | Kollar | 260/348.5 |
| 4,367,342 A | 1/1983 | Wulff et al. | 549/529 |
| 4,410,501 A | 10/1983 | Taramasso et al. | 423/326 |
| 4,833,260 A | 5/1989 | Neri et al. | 549/531 |
| 5,859,265 A | 1/1999 | Muller et al. | 549/531 |
| 6,031,116 A | 2/2000 | Bowman et al. | 549/523 |
| 2003/0204101 A1 | 10/2003 | Jewson et al. | 549/533 |
| 2005/0187394 A1* | 8/2005 | Dessau | 549/533 |

FOREIGN PATENT DOCUMENTS

| | | |
|---|---|---|
| BE | 1001038 A7 | 6/1989 |
| JP | 4-352771 | 12/1992 |
| WO | WO 01/62380 A | 10/2003 |

OTHER PUBLICATIONS

Pirutko, et al., "Preparation And Catalytic Study Of Metal Modified TS-1 In The Oxidation Of Benzene To Phenol By N2O" *Microporous and Mesoporous Materials*, Elsevier Science Publishing, vol. 48, No. 1-3, 2001, no month.

* cited by examiner

*Primary Examiner*—Elizabeth D. Wood
(74) *Attorney, Agent, or Firm*—Kevin M. Carroll

(57) ABSTRACT

Noble metal-containing titanium or vanadium zeolite catalysts are prepared by adding a noble metal source to a titanium or vanadium zeolite that contains templating agent used in the preparation of the zeolite, and then removing the templating agent to form the noble metal-containing titanium or vanadium zeolite catalyst. The catalyst is useful in olefin epoxidation with oxygen and hydrogen.

24 Claims, No Drawings

EPOXIDATION CATALYST

FIELD OF THE INVENTION

This invention relates to a process for producing a noble metal-containing titanium or vanadium zeolite catalyst and its use in olefin epoxidation with oxygen and hydrogen. The process comprises adding a noble metal source to a titanium or vanadium zeolite that still contains the templating agent used in the zeolite synthesis, followed by template removal to form the noble metal-containing titanium or vanadium zeolite catalyst.

BACKGROUND OF THE INVENTION

Many different methods for the preparation of epoxides have been developed. Generally, epoxides are formed by the reaction of an olefin with an oxidizing agent in the presence of a catalyst. The production of propylene oxide from propylene and an organic hydroperoxide oxidizing agent, such as ethyl benzene hydroperoxide or tert-butyl hydroperoxide, is commercially practiced technology. This process is performed in the presence of a solubilized molybdenum catalyst, see U.S. Pat. No. 3,351,635, or a heterogeneous titania on silica catalyst, see U.S. Pat. No. 4,367,342. Hydrogen peroxide is another oxidizing agent useful for the preparation of epoxides. Olefin epoxidation using hydrogen peroxide and a titanium silicate zeolite is demonstrated in U.S. Pat. No. 4,833,260. One disadvantage of both of these processes is the need to pre-form the oxidizing agent prior to reaction with olefin.

Another commercially practiced technology is the direct epoxidation of ethylene to ethylene oxide by reaction with oxygen over a silver catalyst. Unfortunately, the silver catalyst has not proved useful in commercial epoxidation of higher olefins. Therefore, much current research has focused on the direct epoxidation of higher olefins with oxygen and hydrogen in the presence of a catalyst. In this process, it is believed that oxygen and hydrogen react in situ to form an oxidizing agent. Thus, development of an efficient process (and catalyst) promises less expensive technology compared to the commercial technologies that employ pre-formed oxidizing agents.

Many different catalysts have been proposed for use in the direct epoxidation of higher olefins. Typically, the catalyst comprises a noble metal that is supported on a titanosilicate, where the titanosilicate has been calcined prior to noble metal incorporation in order to remove the templating agent used in the titanosilicate synthesis. For example, JP 4-352771 discloses the epoxidation of propylene oxide from the reaction of propylene, oxygen, and hydrogen using a catalyst containing a Group VIII metal such as palladium on a crystalline titanosilicate. U.S. Pat. No. 5,859,265 discloses a catalyst in which a platinum metal, selected from Ru, Rh, Pd, Os, Ir and Pt, is supported on a titanium or vanadium silicalite. Also, U.S. Pat. No. 6,031,116 discloses a gold supported on titanosilicate catalyst. These patents all teach formation of a noble metal-titanosilicate catalyst, wherein the titanosilicate is first calcined to remove templating agent prior to addition of the noble metal.

As with any chemical process, it is desirable to attain still further improvements in the direct epoxidation methods and catalysts. We have discovered an effective, convenient process to form an epoxidation catalyst and its use in the direct epoxidation of olefins with oxygen and hydrogen.

SUMMARY OF THE INVENTION

The invention is a process for producing a noble metal-containing titanium or vanadium zeolite and its use in the epoxidation of olefins with hydrogen and oxygen. The process comprises first adding a noble metal source to a titanium or vanadium zeolite that contains the templating agent used in the zeolite synthesis, and then removing the template to form the noble metal-containing titanium or vanadium zeolite catalyst. The catalyst is active in olefin epoxidation with oxygen and hydrogen.

DETAILED DESCRIPTION OF THE INVENTION

The process of the invention is used to produce noble metal-containing titanium or vanadium zeolites. The noble metal-containing titanium or vanadium zeolites comprise a noble metal and a titanium or vanadium zeolite. Titanium or vanadium zeolites comprise the class of zeolitic substances wherein titanium or vanadium atoms are substituted for a portion of the silicon atoms in the lattice framework of a molecular sieve. Such substances, and their production, are well known in the art. See for example, U.S. Pat. Nos. 4,410,501 and 4,833,260.

The process of the invention uses a titanium or vanadium zeolite that contains the templating agent used in the titanium or vanadium zeolite synthesis. The synthesis of titanium or vanadium zeolites is well known in the art. Titanium or vanadium zeolite synthesis typically comprises reacting a titanium or vanadium compound, a silicon source, and a templating agent at a temperature and for a time sufficient to form a titanium zeolite. Suitable titanium compounds useful in titanium zeolite synthesis include, but are not limited to, titanium alkoxides and titanium halides. Preferred titanium alkoxides are titanium tetraisopropoxide, titanium tetraethoxide and titanium tetrabutoxide. Titanium tetraethoxide is especially preferred. Preferred titanium halides include titanium trichloride and titanium tetrachloride.

Suitable silicon sources include, but are not limited to, colloidal silica, fumed silica and silicon alkoxides. Preferred silicon alkoxides are tetraethylorthosilicate, tetramethylorthosilicate, and the like. Tetraethylorthosilicate is especially preferred.

The templating agent is typically a tetraalkylammonium cation, particularly tetrapropylammonium cation. The templating agent is typically used in the zeolite synthesis as a templating agent compound consisting of the templating agent and an anionic species. The tetraalkylammonium cation is typically used as a hydroxide, halide, nitrate, acetate, and the like compound. Tetraalkylammonium hydroxides and tetraalkylammonium halides, such as tetrapropylammonium hydroxide and tetrapropylammonium halide, are preferred templating agent compounds. Tetrapropylammonium hydroxide is especially preferred.

Synthesis of titanium or vanadium zeolites is carried out by a hydrothermal crystallization of a reaction mixture prepared by combining the titanium or vanadium compound, silicon source, and templating agent compound in the presence of water. Other solvents such as alcohols may also be present. Alcohols such as isopropyl, ethyl and methyl alcohol are preferred, and isopropyl alcohol is especially preferred.

Generally, the hydrothermal process used to prepare titanium or vanadium zeolites involves forming a reaction mixture wherein the molar ratios of additives (as defined in terms of moles of templating agent, moles of $SiO_2$ and moles of $TiO_2$ or $VO_{2.5}$) comprise the following molar ratios: $TiO_2(VO_{2.5})$:$SiO_2$=0.5-5:100; and templating agent: $SiO_2$=10-50:100. The water:$SiO_2$ molar ratio is typically from about 1000-5000:100 and the solvent:$SiO_2$ molar ratio may be in the range of 0-500:100.

The reaction mixture is prepared by mixing the desired sources of titanium or vanadium, silicon and templating agent compound to give the reaction mixture. It is also typically necessary that the mixture have a pH of about 9 to about 13. The basicity of the mixture is controlled by the amount of templating agent compound (if it is in the hydroxide form) which is added and the use of other basic compounds. To increase the basicity of the mixture, more templating agent (hydroxide) compound is typically added to the reaction mixture. If another basic compound is used, the -basic compound is preferably an organic base that is free of alkali metals, alkaline earth metals, and the like. The addition of other basic compounds may be needed if the templating agent is added as a salt, e.g., halide or nitrate. Examples of these basic compounds include ammonium hydroxide, quaternary ammonium hydroxides and amines. Specific examples include tetraethylammonium hydroxide, tetrabutylammonium hydroxide, n-butylamine, and tripropylamine.

After the reaction mixture is formed, it is reacted at a temperature and a time sufficient to form a molecular sieve. Typically, the reaction mixture is heated at a temperature of about 100° C. to about 250° C. for a period of about 0.5 hours to about 96 hours in a sealed vessel under autogenous pressure. Preferably, the reaction mixture is heated at a temperature range from about 125° C. to about 200° C., most preferably from about 150° C. to about 180° C. After the desired reaction time, the titanium or vanadium zeolite is recovered.

Suitable zeolite recovery methods include filtration and washing (typically with deionized water), rotary evaporation, centrifugation, and the like. Preferably, the titanium or vanadium zeolite is washed and then dried. The wash may be useful to remove excess reagents from the zeolite after crystallization step. Although any suitable wash solvent may be used, the wash is preferably performed using water or an aqueous acidic solution. The aqueous acidic solution may be a mineral or organic acid solution. The titanium or vanadium zeolite may additionally be dried at a temperature greater than about 20° C., preferably from about 50° C. to about 200° C. As recovered, the titanium or vanadium zeolite still contains the templating agent that was used in the zeolite synthesis.

The titanium zeolite useful in the invention preferably is of the class of molecular sieves commonly referred to as titanium silicalites, particularly "TS-1" (having an MFI topology analogous to that of the ZSM-5 aluminosilicate zeolites), "TS-2" (having an MEL topology analogous to that of the ZSM-11 aluminosilicate zeolites), and "TS-3" (as described in Belgian Pat. No. 1,001,038). Titanium-containing molecular sieves having framework structures isomorphous to zeolite beta, mordenite, ZSM-48, ZSM-12, and MCM-41 may used in the process of the invention.

According to the process of the invention, a noble metal source is added to the titanium or vanadium zeolite that still contains the templating agent used in the titanium or vanadium zeolite synthesis. The titanium or vanadium zeolite may be in the form of a powder or a large particle size solid. For instance, the titanium or vanadium zeolite may be spray dried, pelletized or extruded prior to noble metal incorporation. If spray dried, pelletized or extruded, the titanium or vanadium zeolite may additionally comprise a binder or the like and may be molded, spray dried, shaped or extruded into any desired form prior noble metal incorporation.

The noble metal source comprises a compound or complex of palladium, platinum, gold, silver, iridium, rhenium, ruthenium, osmium, or mixtures thereof. Palladium, platinum, and gold are particularly desirable; palladium is most preferred. There are no particular restrictions regarding the choice of noble metal compound or complex used as the source of the noble metal. For example, suitable compounds for such purpose include the nitrates, sulfates, halides (e.g., chlorides, bromides), carboxylates (e.g., acetate), and amine complexes of noble metals, as well as compounds containing a mixture of such ligands.

The typical amount of noble metal present in the noble metal-containing titanium or vanadium zeolite will be in the range of from about 0.001 to 10 weight percent, preferably 0.005 to 5 weight percent, and particularly 0.01 to 1 weight percent. The manner in which the noble metal is incorporated into the catalyst is not considered to be particularly critical. For example, the noble metal may be supported on the zeolite by impregnation, adsorption, precipitation or the like. Alternatively, the noble metal can be incorporated into the zeolite by ion-exchange with, for example, a tetraammine palladium salt such as tetraammine palladium dinitrate, dihalide or sulfate.

Following noble metal incorporation, the addition product of noble metal and titanium or vanadium zeolite will still contain some of the templating agent in the zeolite pores. The process of the invention also comprises removing the templating agent to form the noble metal-containing titanium or vanadium zeolite. If the addition product of noble metal and titanium or vanadium zeolite is produced in the form of a powder, it may be spray dried, pelletized or extruded prior to the templating agent removal step. If spray dried, pelletized or extruded, the addition product may additionally comprise a binder or the like and may be molded, spray dried, shaped or extruded into any desired form prior the templating agent removal step.

Any suitable method to remove the templating agent may be employed. The template removal may be performed by a thermal treatment in the presence of inert gas, by an oxidative treatment under conditions that decompose the templating agent, or by a combination of both. Oxidation may be conducted in the presence of oxygen, ozone, $NO_x$, or combinations thereof. The zeolite may also be contacted with an oxidant such as hydrogen peroxide (or hydrogen and oxygen to form hydrogen peroxide in situ), organic hydroperoxides, or peracids to remove the templating agent. Alternatively, the zeolite may be contacted with an enzyme, or may be exposed to an energy source such as microwaves or light in order to decompose the templating agent.

Preferably, the addition product of noble metal and titanium or vanadium zeolite is heated at temperatures greater than 250° C. following noble metal incorporation to remove the templating agent. Temperatures of from about 275° C. to about 800° C. are preferred, and most preferably from about 300° C. to about 600° C. The high temperature heating may be conducted in inert atmosphere which is substantially free of oxygen, such as nitrogen, argon, neon, helium or the like or mixture thereof. By "substantially free of oxygen", it is meant that the inert atmosphere contains less than 10,000 ppm mole oxygen, preferably less than 2000 ppm. Also, the heating may be conducted in an oxygen-containing atmosphere, such as air or a mixture of oxygen and an inert gas. Alternatively, the catalyst may also be heated in the presence of an inert gas such as nitrogen prior to heating in an oxygen-containing atmosphere. The heating process may be conducted such that the gas stream (inert, oxygen-containing, or both) is passed over the noble metal-containing titanium or vanadium zeolite. Alternatively, the heating may be performed in a static manner. The zeolite could also be agitated or stirred while being contacted with the gas stream.

Following the heating step, the noble metal-containing titanium or vanadium zeolite is preferably reduced at a temperature of at least 20° C. in the presence of molecular hydrogen, but preferably at least 30° C. The temperature range of from 40° C. to 150° C. is especially suitable. The molecular hydrogen may be combined with other gases such as nitrogen and the like. The percent molecular hydrogen in the gas stream should be selected so that excessive or uncontrollable exotherms are not produced. Typically, the gas stream will comprise from about 1 to 30 volume percent hydrogen. The process may be conducted such that a gas stream comprising molecular hydrogen is passed over the heated zeolite. Alternatively, the reduction may be performed in a static manner. The heated zeolite could also be agitated or stirred while being contacted with the hydrogen-containing gas.

The noble metal-containing titanium or vanadium zeolite is useful for catalyzing the epoxidation of olefins with oxygen and hydrogen. This epoxidation process comprises contacting an olefin, oxygen, and hydrogen in the presence of the noble metal-containing titanium or vanadium zeolite. In addition to the noble metal-containing titanium or vanadium zeolite, additional palladium-free titanium or vanadium zeolite may be used in the epoxidation process. The palladium-free titanium or vanadium zeolite is a titanium or vanadium-containing molecular sieve that is free of added palladium. The addition of a palladium-free titanium or vanadium zeolite has proven beneficial to productivity of the palladium that is present in the catalyst.

Suitable olefins include any olefin having at least one carbon-carbon double bond, and generally from 2 to 60 carbon atoms. Preferably the olefin is an acyclic alkene of from 2 to 30 carbon atoms; the process of the invention is particularly suitable for epoxidizing $C_2$-$C_6$ olefins. More than one double bond may be present, as in a diene or triene for example. The olefin may be a hydrocarbon (i.e., contain only carbon and hydrogen atoms) or may contain functional groups such as halide, carboxyl, hydroxyl, ether, carbonyl, cyano, or nitro groups, or the like. The process of the invention is especially useful for converting propylene to propylene oxide.

Oxygen and hydrogen are also required for the epoxidation process. Although any sources of oxygen and hydrogen are suitable, molecular oxygen and molecular hydrogen are preferred.

Epoxidation according to the invention is carried out at a temperature effective to achieve the desired olefin epoxidation, preferably at temperatures in the range of 0-250° C., more preferably, 20-100° C. The molar ratio of hydrogen to oxygen can usually be varied in the range of $H_2$:$O_2$=1:10 to 5:1 and is especially favorable at 1:5 to 2:1. The molar ratio of oxygen to olefin is usually 2:1 to 1:20, and preferably 1:1 to 1:10. A carrier gas may also be used in the epoxidation process. As the carrier gas, any desired inert gas can be used. The molar ratio of olefin to carrier gas is then usually in the range of 100:1 to 1:10 and especially 20:1 to 1:10.

As the inert gas carrier, noble gases such as helium, neon, and argon are suitable in addition to nitrogen and carbon dioxide. Saturated hydrocarbons with 1-8, especially 1-6, and preferably with 1-4 carbon atoms, e.g., methane, ethane, propane, and n-butane, are also suitable. Nitrogen and saturated $C_1$-$C_4$ hydrocarbons are the preferred inert carrier gases. Mixtures of the listed inert carrier gases can also be used.

Specifically in the epoxidation of propylene, propane can be supplied in such a way that, in the presence of an appropriate excess of carrier gas, the explosive limits of mixtures of propylene, propane, hydrogen, and oxygen are safely avoided and thus no explosive mixture can form in the reactor or in the feed and discharge lines.

Depending on the olefin to be reacted, the epoxidation according to the invention can be carried out in the liquid phase, the gas phase, or in the supercritical phase. When a liquid reaction medium is used, the catalyst is preferably in the form of a suspension or fixed-bed. The process may be performed using a continuous flow, semi-batch or batch mode of operation.

If epoxidation is carried out in the liquid (or supercritical) phase, it is advantageous to work at a pressure of 1-100 bars and in the presence of one or more solvents. Suitable solvents include, but are not limited to, alcohols, water, supercritical $CO_2$, or mixtures thereof. Suitable alcohols include $C_1$-$C_4$ alcohols such as methanol, ethanol, isopropanol, and tert-butanol, or mixtures thereof. Fluorinated alcohols can be used. It is preferable to use mixtures of the cited alcohols with water.

If epoxidation is carried out in the liquid (or supercritical) phase, it is advantageous to use a buffer. The buffer will typically be added to the solvent to form a buffer solution. The buffer solution is employed in the reaction to inhibit the formation of glycols or glycol ethers during epoxidation. Buffers are well known in the art.

Buffers useful in this invention include any suitable salts of oxyacids, the nature and proportions of which in the mixture, are such that the pH of their solutions may range from 3 to 10, preferably from 4 to 9 and more preferably from 5 to 8. Suitable salts of oxyacids contain an anion and cation. The anion portion of the salt may include anions such as phosphate, carbonate, bicarbonate, carboxylates (e.g., acetate, phthalate, and the like), citrate, borate, hydroxide, silicate, aluminosilicate, or the like. The cation portion of the salt may include cations such as ammonium, alkylammoniums (e.g., tetraalkylammoniums, pyridiniums, and the like), alkali metals, alkaline earth metals, or the like. Cation examples include $NH_4$, $NBu_4$, $NMe_4$, Li, Na, K, Cs, Mg, and Ca cations. More preferred buffers include alkali metal phosphate and ammonium phosphate buffers. Buffers may preferably contain a combination of more than one suitable salt. Typically, the concentration of buffer in the solvent is from about 0.0001 M to about 1 M, preferably from about 0.001 M to about 0.3 M. The buffer useful in this invention may also include the addition of ammonia gas to the reaction system.

The following examples merely illustrate the invention. Those skilled in the art will recognize many variations that are within the spirit of the invention and scope of the claims.

EXAMPLE 1

Preparation of Pd/TS-1 Catalysts

Comparative Example 1A: Spray dried TS-1 (100 g, 80% TS-1, silica binder, 1.3 wt. % Ti, C<0.1 wt. %, N<0.1 wt. %, H<0.1 wt. %, calcined 550° C. in air, 50 micron size weighted by volume) is slurried in deionized water (180 g) and the pH is taken (5.38). After mixing for 5 minutes, an aqueous solution of tetra ammine palladium dinitrate (2.1 g aqueous solution containing 5.37 wt. % Pd, further diluted with 20 g of deionized water) is added with mixing over 5 minutes. After mixing for 10 minutes, the pH is adjusted from 5.49 to 7.53 with 5 wt. % aqueous ammonium hydroxide and the slurry is agitated at 30° C. for 0.5 hour. The pH is then adjusted from 7.35 to 7.49. The slurry is filtered and the filter cake is washed three times by reslurrying in deionized water (150 g) and filtering again. The solids are air dried overnight and then dried in a vacuum oven at 50° C. for 16 hours. The dried solid contains 0.1 wt. % Pd and 1.3 wt. % Ti.

The dried solids are oven calcined in air by heating from 23 to 110° C. at 10° C./min and holding at 110° C. for 2 hours, then heating to 300° C. at 2° C./min and holding at 300° C. for 4 hours. The calcined solids are then transferred to a quartz tube, heated to 50° C. and treated with 5 vol. % hydrogen in nitrogen (100 cc/min) for 4 hours. After the hydrogen treatment, nitrogen is passed through the solids for 1 hour before cooling to 23° C. and recovering the catalyst.

Example 1B: The spray dried TS-1 used in Comparative Example 1A (23 g, not calcined at 550° C. in air, 7.5 wt. % C, 1.21 wt. % H, 0.5 wt. % N) is slurried in deionized water (46 g) and the pH is taken (6.04). After mixing for 5 minutes, an aqueous solution of tetra ammine palladium dinitrate (0.42 g aqueous solution containing 5.37 wt. % Pd, further diluted with 3.0 g of deionized water) is added with mixing over 5 minutes. After mixing for 10 minutes, the pH is then adjusted from 7.11 to 7.63 with 5 wt. % aqueous ammonium hydroxide and the slurry is agitated at 30° C. for 0.5 hour. The slurry is filtered and the filter cake is washed three times by reslurrying in deionized water (40 g) and filtering again. The solids are air dried overnight and then dried in a vacuum oven at 50° C. for 16 hours. The dried solid contains 0.09 wt. % Pd, 1.3 wt. % Ti, 7.5 wt. % C, 0.5 wt. % N, and 1.21 wt. % H).

The dried solids are then transferred to a quartz tube, heated under nitrogen flow (100 cc/min) at 1100° C. for 1 hour, 450° C. for 3 hour and then cooled to 23° C. The resulting solids contain 1.3 wt. % Ti, 0.1 wt. % Pd, 0.39 wt. % C, and <0.1 wt. % H and N. The nitrogen treated solids are oven calcined in air by heating from 23 to 110° C. at 10° C./min and holding at 110° C. for 2 hours, then heating to 300° C. at 2° C./min and holding at 300° C. for 4 hours. The calcined catalyst contained 0.1 wt. % Pd and C=0.26 wt. %. The calcined solids are then transferred to a quartz tube, heated to 50° C. and treated with 5 vol. % hydrogen in nitrogen (100 cc/min) for 4 hours. After the hydrogen treatment, nitrogen is passed through the solids for 1 hour before cooling to 23° C. and recovering the Catalyst 1B.

Example 1C: Catalyst 1C is made according to the same procedure as Catalyst 1B except that the dried solids are oven calcined in air by heating from 23 to 110° C. at 10° C./min and holding at 110° C. for 2 hours, then heating to 300° C. at 2° C./min and holding at 300° C. for 4 hours. The calcined catalyst contained 0.1 wt. % Pd and 1.15 wt. % C. The calcined solids are then transferred to a quartz tube, heated to 50° C. and treated with 5 vol. % hydrogen in nitrogen (100 cc/min) for 4 hours. After the hydrogen treatment, nitrogen is passed through the solids for 1 hour before cooling to 23° C. and recovering the catalyst.

Comparative Example 1D: Powder TS-1 (12 g, 80% TS-1, silica binder, 2.6 wt. % Ti, calcined at 550° C. in air, C<0.1 wt. %, particle size=0.3 micron) is slurried in deionized water (24 g) and the pH is adjusted from 4.81 to 7.34 using 5 wt. % aqueous ammonium hydroxide. After mixing for 5 minutes, an aqueous solution of tetra ammine palladium dinitrate (0.22 g aqueous solution containing 5.37 wt. % Pd, further diluted with 1.0 g of deionized water) is added with mixing over 1 minute. The pH is then adjusted from 6.1 to 7.3 with 5 wt. % aqueous ammonium hydroxide and the slurry is agitated at 30° C. for 10 minutes. The pH is adjusted from 6.68 to 7.29 and agitated at 30° C. for 20 minutes. The pH is adjusted from 7.0 to 7.33 with 5 wt. % aqueous ammonium hydroxide. The slurry is filtered and the filter cake is washed three times by reslurrying in deionized water (25 g) and filtering again. The solids are then air dried overnight and dried in a vacuum oven at 50° C. for 16 hours. The dried solid contains 0.1 wt. % Pd and 2.6 wt. % Ti.

The dried solids are then transferred to a quartz tube, heated at 550° C. for 4 hours under nitrogen flow (100 cc/min), and then cooled to 23° C. The resulting solids contains 2.6 wt. % Ti, 0.1 wt. % Pd, and <0.1 wt. % C, H, and N. The nitrogen treated solids are oven calcined in air by heating from 23 to 110° C. at 10° C./min and holding at 110° C. for 2 hours, then heating to 550° C. at 2° C./min and holding at 550° C. for 4 hours. The calcined solids are then transferred to a quartz tube, heated to 100° C. and treated with 5 vol. % hydrogen in nitrogen (100 cc/min) for 4 hours. After the hydrogen treatment, nitrogen is passed through the solids for 1 hour before cooling to 23° C. and recovering the catalyst.

Example 1E: The powder TS-1 used in Comparative Example 1D (24 g, not calcined in air, 9.3 wt. % C, 0.71 wt. % N, 1.53 wt. % H) is slurried in deionized water (48 g) and the pH is adjusted from 5.34 to 7.39 using 5 wt. % aqueous ammonium hydroxide. After mixing for 5 minutes, an aqueous solution of tetra ammine palladium dinitrate (0.44 g aqueous solution containing 5.37 wt. % Pd, further diluted with 1.0 g of deionized water) is added with mixing over 1 minute. The pH is 7.48 and the slurry is agitated at 30° C. for 10 minutes. The pH is then adjusted from 7.14 to 7.42 with 5 wt. % ammonium hydroxide and the slurry is agitated at 30° C. for 20 minutes. The pH is adjusted form 7.25 to 7.39 with 5 wt. % aqueous ammonium hydroxide and the slurry is filtered and the filter cake washed three times by reslurrying in deionized water (50 g) and filtering again. The solids are then air dried overnight and dried in a vacuum oven at 50° C. for 16 hours. The dried solid contains 0.1 wt % Pd and 2.4 wt. % Ti.

The dried solids are transferred to a quartz tube, heated at 550° C. under nitrogen flow (100 cc/min) for 4 hours, and then cooled to 23° C. Resulting Catalyst 1E contains 2.4 wt. % Ti, 0.11 wt. % Pd, 0.44 wt. % C, <0.1 wt. % H and N.

Example 1F: Catalyst 1F is made according to the same procedure as Catalyst 1E except that the Catalyst 1E is further oven calcined in air by heating from 23 to 110° C. at 10° C./min and holding at 110° C. for 2 hours, then heating to 550° C. at 2° C./min and holding at 550° C. for 4 hours. The calcined solids are then transferred to a quartz tube, heated to 100° C. and treated with 5 vol. % hydrogen in nitrogen (100 cc/min) for 4 hours. After the hydrogen treatment, nitrogen is passed through the solids for 1 hour before cooling to 23° C. and recovering Catalyst 1F.

EXAMPLE 2

Epoxidation of Propylene

A 300 cc stainless steel reactor is charged with 0.7 grams of catalyst from Example 1 (0.7 g), methanol (100 g), and a 0.1 M aqueous ammonium phosphate solution at a measured pH of 6.0 (13 g). The reactor is then charged to 300 psig of a feed consisting of hydrogen (2 vol. %), oxygen (4 vol. %), propylene (5 vol. %), methane (0.5 vol. %), and the balance nitrogen. The pressure in the reactor is maintained at 300 psig via a back pressure regulator with the feed gases passed continuously through the reactor at 1600 cc/min (measured at 23° C. and one atmosphere pressure). In order to maintain a constant solvent level in the reactor during the run, the oxygen, nitrogen and propylene feeds are first passed through a two-liter stainless steel vessel (saturator) containing 1.5 liters of methanol prior to the reactor. The reactor is stirred at 1500 rpm and the reaction mixture is heated to 60° C. The gaseous effluent is analyzed by an online GC every hour and the liquid analyzed by is offline GC at the end of the 18 hour run. Propylene oxide and equivalents ("POE"), which include propylene oxide ("PO"), propylene glycol, and glycol ethers, are produced during the reaction, in addition to propane formed by the hydrogenation of propylene. The results of the GC analyses are used to calculate the selectivities shown in Table 1.

The results demonstrate that it is not necessary to remove the template from the titanium zeolite prior to noble metal deposition. In fact, the results show comparable productivity and PO/POE selectivity for catalysts produced by depositing noble metal on a titanium zeolite that still contained the templating agent used in the zeolite synthesis.

TABLE 1

COMPARISON OF CATALYST ACTIVITY AND SELECTIVITY

| Catalyst | TS-1 Pre-Treatment prior to Pd deposition | Catalyst Treatment after Pd deposition | Wt. % Pd | Productivity[1] | PO/POE Selectivity (%)[2] |
|---|---|---|---|---|---|
| 1A* | Calcined at 550° C. to remove template | Air at 300° C.; $H_2$ at 50° C. | 0.1 | 0.24 | 93 |
| 1B | — | $N_2$ at 450° C.; Air at 300° C.; $H_2$ at 50° C. | 0.09 | 0.24 | 94 |
| 1C | — | Air at 300° C.; $H_2$ at 50° C. | 0.09 | 0.22 | 94 |
| 1D* | Calcined at 550° C. to remove template | $N_2$ at 550° C.; Air at 550° C.; $H_2$ at 100° C. | 0.09 | 0.4 | 90 |
| 1E | — | $N_2$ at 550° C. | 0.11 | 0.41 | 89 |
| 1F | — | $N_2$ at 550° C.; Air at 550° C.; $H_2$ at 100° C. | 0.1 | 0.41 | 90 |

*Comparative Example
[1]Productivity = grams POE produced/gram of catalyst per hour.
[2]PO/POE Selectivity = moles PO/(moles PO + moles glycols + moles glycol ethers) * 100.

I claim:

1. A process comprising:
   (a) adding a noble metal source to a titanium or vanadium zeolite containing a templating agent to form an addition product; and
   (b) removing the templating agent from the addition product to form a noble metal-containing titanium or vanadium zeolite.

2. The process of claim 1 wherein the templating agent is a tetraalkylammonium.

3. The process of claim 1 wherein the templating agent is removed by heating the addition product at a temperature greater than 250° C.

4. The process of claim 3 wherein the addition product is heated in an inert atmosphere.

5. The process of claim 3 wherein the addition product is heated in the presence of a gas stream comprising oxygen.

6. The process of claim 3 wherein the addition product is first heated in an inert atmosphere and then heated in the presence of a gas stream comprising oxygen.

7. The process of claim 3 wherein the noble metal-containing titanium or vanadium zeolite is reduced at a temperature of at least 20° C. in the presence of a gas stream comprising hydrogen.

8. The process of claim 1 wherein the noble metal source comprises one or more noble metals selected from the group consisting of palladium, platinum, gold, silver, iridium, rhenium, ruthenium, and osmium.

9. The process of claim 1 wherein the noble metal source comprises palladium.

10. The process of claim 9 wherein the palladium is added to the titanium or vanadium zeolite containing a templating agent by ion exchange with a tetraammine palladium salt.

11. The process of claim 1 wherein the noble metal-containing titanium zeolite comprises a titanium silicalite and one or more noble metals selected from the group consisting of palladium, platinum, and gold.

12. The process of claim 11 wherein the titanium silicalite is TS-1 or TS-2.

13. A process comprising:
   (a) adding a palladium source to a titanium silicalite containing a tetraalkylammonium templating agent to form an addition product; and
   (b) heating the addition product at a temperature greater than 250° C. in an inert atmosphere, a gas stream comprising oxygen, or in an inert atmosphere followed by a gas stream comprising oxygen to form a palladium-containing titanium silicalite.

14. The process of claim 13 wherein the palladium-containing titanium silicalite is further reduced at a temperature of at least 20° C. in the presence of a gas stream comprising hydrogen.

15. The process of claim 13 wherein the titanium silicalite is TS-1 or TS-2.

16. A process comprising reacting an olefin, hydrogen, and oxygen in the presence of a noble metal-containing titanium or vanadium zeolite, wherein the noble metal-containing titanium or vanadium zeolite is produced by:

(a) adding a noble metal source to a titanium or vanadium zeolite containing a templating agent to form an addition product; and (b) removing the templating agent from the addition product.

17. The process of claim 16 wherein the templating agent is a tetrasikylammonium.

18. The process of claim 16 wherein the templating agent is removed by heating the addition product at a temperature greater than 250° C. in an inert atmosphere, a gas stream comprising oxygen, or in an inert atmosphere followed by a gas stream comprising oxygen.

19. The process of claim 18 wherein the noble metal-containing titanium or vanadium zeolite is further reduced at a temperature of at least 20° C. in the presence of a gas stream comprising hydrogen.

20. The process of claim 16 wherein the noble metal source comprises one or more noble metals selected from the group consisting of palladium, platinum, gold, silver, iridium, rhenium, ruthenium, and osmium.

21. The process of claim 16 wherein the noble metal source comprises one or more noble metals selected from the group consisting of palladium, platinum, and gold.

22. The process of claim 16 wherein the titanium zeolite comprises a titanium silicalite.

23. The process of claim 16 wherein the olefin is a $C_2$-$C_6$ olefin.

24. The process of claim 16 wherein the olefin is propylene and propylene oxide is formed.

* * * * *